United States Patent
Sanfilippo, II

(12) 
(10) Patent No.: US 6,468,252 B1
(45) Date of Patent: Oct. 22, 2002

(54) CLAMP FOR VASCULAR ACCESS DEVICE

(76) Inventor: Dominic J. Sanfilippo, II, 9157 - 28th St., Ada, MI (US) 49301

( * ) Notice: Subject to any disclaimer, the term of this patent is extended or adjusted under 35 U.S.C. 154(b) by 85 days.

(21) Appl. No.: 09/631,847

(22) Filed: Aug. 3, 2000

(51) Int. Cl.⁷ .......................... A61K 9/02; A61M 31/00; A61B 17/20

(52) U.S. Cl. ............................ 604/288.01; 604/288.04; 604/22

(58) Field of Search .................. 604/93.01, 288.01, 604/288.02, 288.04, 171, 22, 285

(56) References Cited

U.S. PATENT DOCUMENTS

| | | | |
|---|---|---|---|
| 1,267,250 A | 5/1918 | Murry | |
| 3,825,001 A | * 7/1974 | Bennet et al. | 128/214.4 |
| 4,256,106 A | 3/1981 | Shoor | 128/247 |
| 4,260,181 A | 4/1981 | Curtin | 285/15 |
| 4,364,387 A | 12/1982 | Larkin | 128/214 |
| 4,369,781 A | * 1/1983 | Gilson et al. | 128/214 R |
| 4,405,312 A | 9/1983 | Gross | 604/29 |
| 4,417,890 A | 11/1983 | Dennehey | 604/256 |
| 4,432,759 A | 2/1984 | Gross | 604/411 |
| 4,473,369 A | 9/1984 | Lueders | 604/244 |
| RE31,855 E | 3/1985 | Osborne | 604/161 |

(List continued on next page.)

FOREIGN PATENT DOCUMENTS

| | | |
|---|---|---|
| DE | 2721340 | 11/1978 |
| GB | 1136512 | 12/1968 |

*Primary Examiner*—William C. Doerrler
(74) *Attorney, Agent, or Firm*—Van Dyke, Gardner, Linn & Burkhart, LLP

(57) ABSTRACT

A vascular access device is provided which comprises an implant body and a delivery tube coupled to a cannula of the body for delivering the medical treatment to a preselected site in a patient's body, which permits subcutaneous implanting of the device with a minimally invasive procedure. The body includes an insertion end which is formed by a clamp, with the clamp sealing the tube onto the cannula. The clamp preferably comprises a pair of clamp halves which define a transverse opening in which the tube is clamped on to the cannula. Once the tube is clamped onto the cannula, the clamp halves are preferably secured together, for example, by welding or an adhesive or the like.

40 Claims, 7 Drawing Sheets

U.S. PATENT DOCUMENTS

| | | | | |
|---|---|---|---|---|
| 4,504,269 A | | 3/1985 | Durand | 604/272 |
| 4,673,394 A | | 6/1987 | Fenton, Jr. | 604/175 |
| 4,692,146 A | | 9/1987 | Hilger | 604/93 |
| 4,710,167 A | | 12/1987 | Lazorthes | 604/93 |
| 4,723,948 A | | 2/1988 | Clark | 604/283 |
| 4,741,559 A | | 5/1988 | Berghman | 285/45 |
| 4,751,926 A | | 6/1988 | Saski | 128/303 |
| 4,767,410 A | | 8/1988 | Moden | 604/175 |
| 4,776,839 A | | 10/1988 | Doumenis | 604/9 |
| 4,826,480 A | | 5/1989 | Diaz | 604/49 |
| 4,840,190 A | | 6/1989 | Sasaki | 128/897 |
| 4,865,818 A | | 9/1989 | Merry | 422/179 |
| 5,026,344 A | * | 6/1991 | Dijkstra et al. | 604/93 |
| 5,053,031 A | | 10/1991 | Borsanyi | 604/891.1 |
| 5,084,015 A | | 1/1992 | Moriuchi | 604/96 |
| 5,085,644 A | | 2/1992 | Watson | 604/153 |
| 5,090,954 A | | 2/1992 | Geary | 604/29 |
| 5,167,638 A | | 12/1992 | Felix | 604/175 |
| 5,178,612 A | | 1/1993 | Fenton, Jr. | 604/283 |
| 5,261,885 A | | 11/1993 | Lui | 604/247 |
| 5,281,205 A | | 1/1994 | McPherson | 604/267 |
| 5,360,407 A | | 11/1994 | Leonard | 604/175 |
| 5,387,192 A | | 2/1995 | Glantz | 604/93 |
| 5,409,454 A | * | 4/1995 | Fischell et al. | 604/22 |
| 5,458,380 A | | 10/1995 | Kanao | 285/369 |
| 5,480,193 A | | 1/1996 | Echols | 285/45 |
| 5,484,409 A | | 1/1996 | Atkinson | 604/96 |
| 5,531,684 A | | 7/1996 | Ensminger | 604/93 |
| 5,531,695 A | | 7/1996 | Swisher | 604/111 |
| 5,558,641 A | | 9/1996 | Glantz | 604/93 |
| 5,562,617 A | | 10/1996 | Finch, Jr. | 604/93 |
| 5,688,237 A | | 11/1997 | Rozga | 604/53 |
| 5,738,384 A | | 4/1998 | Boehme | 285/114 |
| 5,741,228 A | | 4/1998 | Lambrecht | 604/93 |
| RE35,841 E | | 7/1998 | Frank | 604/256 |
| 5,895,076 A | | 4/1999 | Elliott | 285/14 |
| 5,919,160 A | | 7/1999 | Sanfilippo | 604/93 |
| 6,013,058 A | | 1/2000 | Prosl | 604/167 |
| 6,039,712 A | | 3/2000 | Fogarty | 604/93 |
| 6,235,042 B1 | * | 5/2001 | Katzman | 606/159 |

* cited by examiner

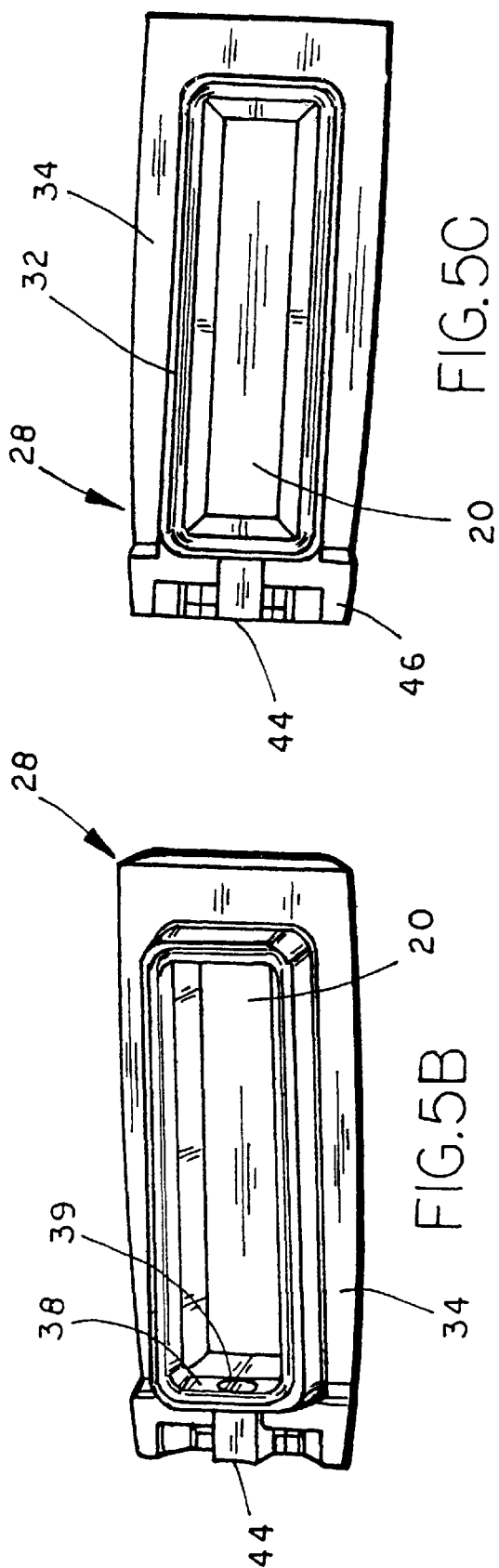
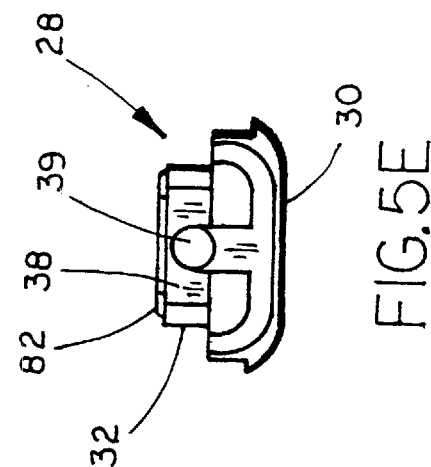
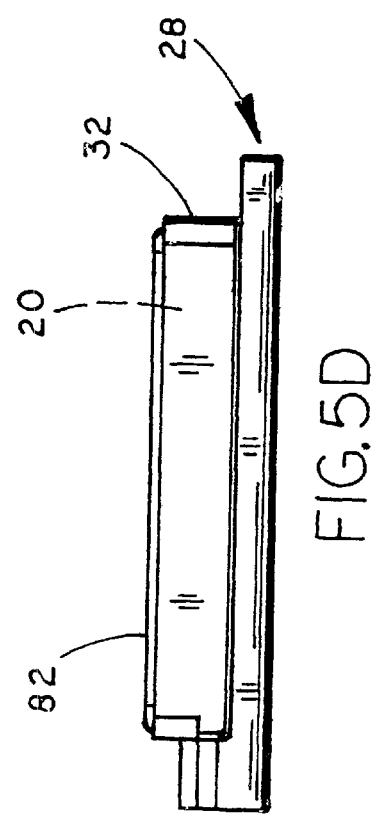

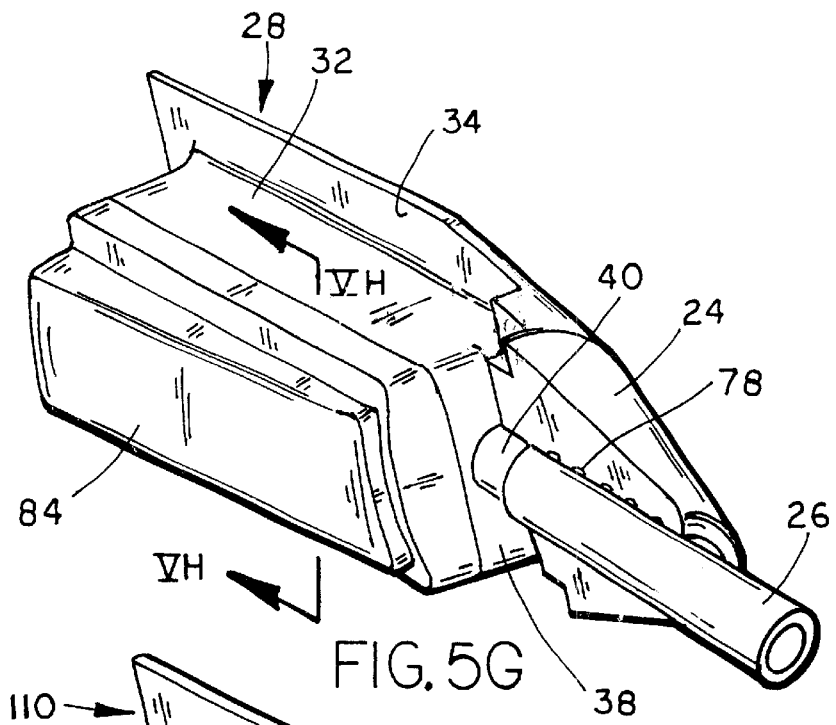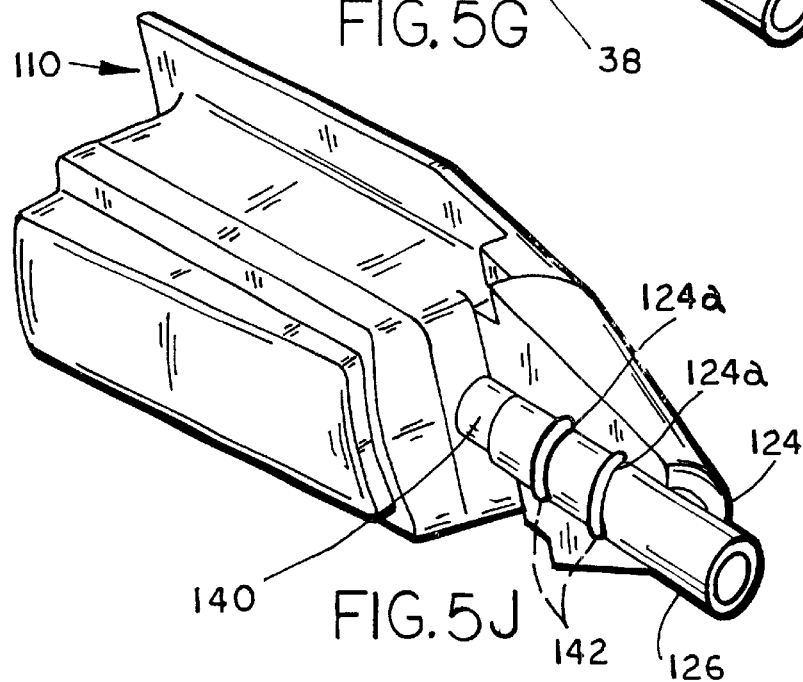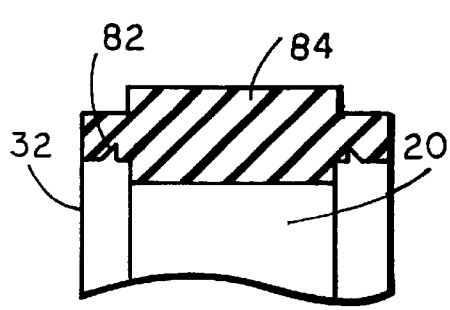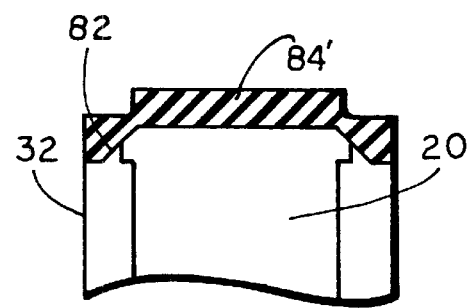

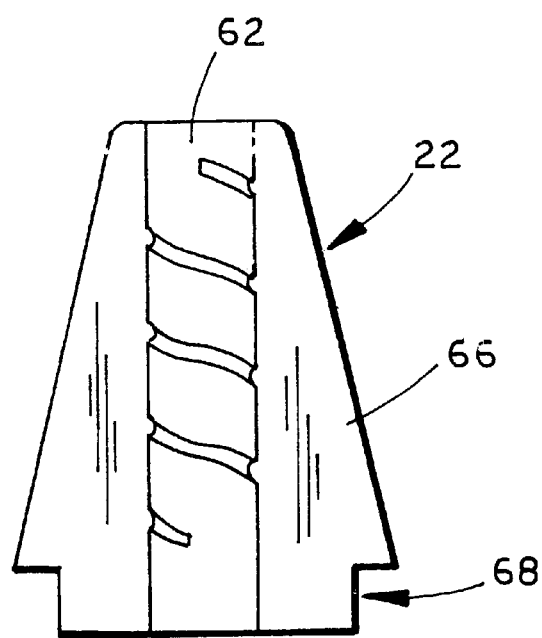
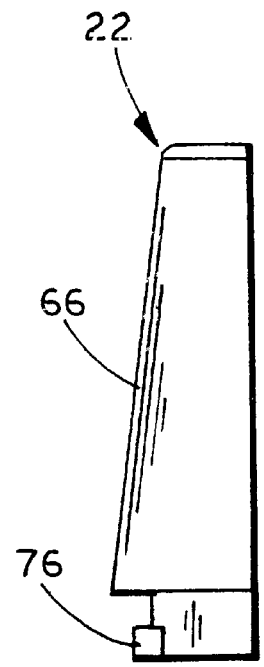
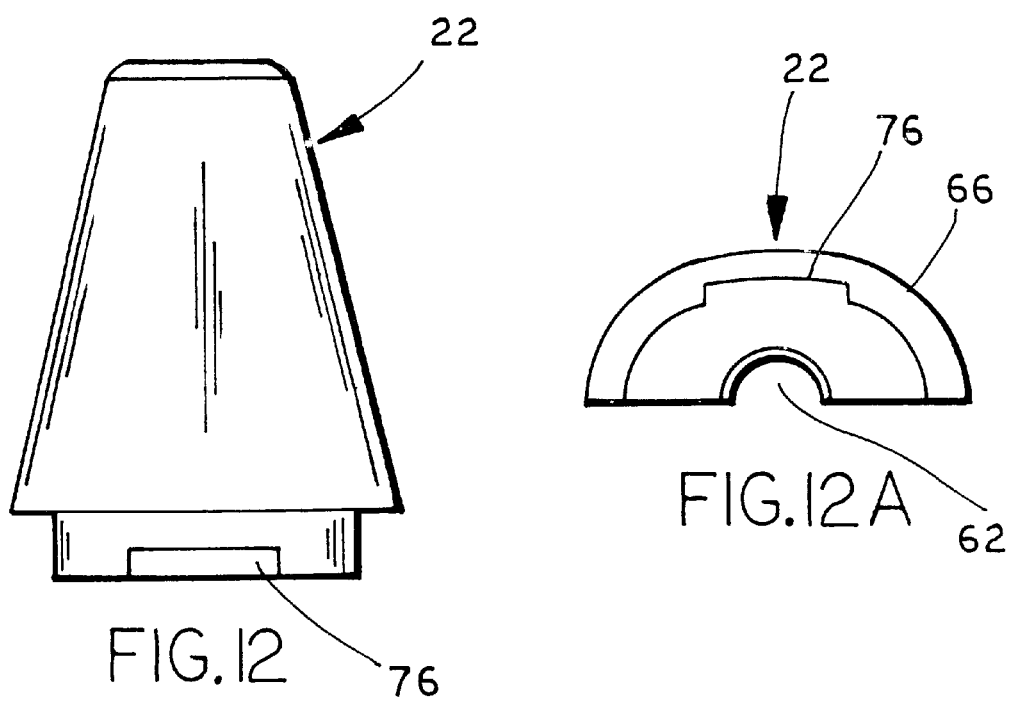
FIG. 10  FIG. 11  FIG. 12  FIG. 12A

CLAMP FOR VASCULAR ACCESS DEVICE

TECHNICAL FIELD AND BACKGROUND OF THE INVENTION

This invention relates to vascular access systems implanted in individuals for the infusion of medication and the like, and particularly to vascular access systems which permit repeated introduction of medication into the device with minimal tissue damage to the individual.

In the treatment of many illnesses, it is necessary to repeatedly infuse medication directly into the bloodstream, into a particular organ, or otherwise to a particular medication site. For example, various chemotherapy regimes for treatment of cancerous conditions require frequent periodic medication. Bowel diseases and bone infections are other examples of conditions which require repeated treatment, as does the periodic dispensing of pain medication for terminally ill patients. In such frequent medication situations, to avoid having to locate a blood vessel for injection by a needle each time, various implantable devices have been developed to administer medications, including, for example external extending catheters, such as those referred to as BROVIAC, GROSHONG, and HICKMAN catheters. While there are differences between these external extending catheters, in the medical trade these various catheters are generally collectively referred to as BROVIAC-type catheters, or "BROVIACS." Often, the medication is toxic in concentrated amounts and, therefore, must be infused through the catheter into a large volume of blood, such as through a large vein or a chamber in the heart. To accomplish this, one end of the catheter is fed through a vessel to a large vein or a chamber of the heart while the other end of the catheter projects through the patient's skin to permit medication to be injected into the catheter. Typically, the externally extending catheters are implanted using a guide wire, which is inserted into the body and directed to the point of application through the cannula of a large needle. Once the guide wire is in place in the body, a sheath is fitted on a dilator and guided down the guide wire by the dilator. When the dilator is withdrawn, the sheath forms a tunnel through the body to the point of application. The distal end of the catheter is then directed to the point of application through the sheath, leaving the proximate end of the catheter extending from the body. The sheath is formed from peel away sections, which are separated to remove the sheath and leave the catheter extending into the body to the selected treatment site.

Another prior art technique of installing a catheter is referred to as a direct cutdown technique, in which an incision is made over the vein and the catheter is then inserted directly into the vein without use of a guide wire. The tunnel may be formed using a second cutdown or skin incision and a sharp tipped hollow metal trocar tunneling device.

An advantage of the externally extending catheters is that they can be inserted under light anesthesia on an outpatient basis. Furthermore, they tend to require non-invasive procedures, requiring only a small incision in the skin. Moreover, the procedure is relatively quick. An external extending catheter can be implanted or removed in a matter of fifteen minutes or thereabouts. Moreover, the externally extending catheter can be used for numerous applications, such as chemotherapy, treatment of bowel disease, blood product infusions, bone infection, and can be used to administer pain medicines for terminally ill or seriously injured persons.

A problem that arises with some implanted vascular access systems is that, despite steps taken after they are used to keep them clean, the catheter may become infected. Given sufficient time, any catheter system which leaves the access opening external of the body will necessarily develop infection at the site where the catheter passes through the skin. However, as described, disadvantages of the externally extending catheter include a significant likelihood of infection at the point of exit from the body. In addition, the protruding catheters have the added disadvantage of creating an unsightly and somewhat intimidating medical device that protrudes from the body, and, as a result, has the added disadvantage of placing a restriction on the patient's activities. The patient cannot swim or engage in numerous other activities that would expose the catheter exit site to an even greater risk of infection.

Another general type of system which is implanted is generally referred to as a vascular port, such as, for example, PORT-A-CATH ®, available from Pharmacia Deltec, Inc., in St. Paul, Minn., or as disclosed in U.S. Pat. No. 5,281,205 to McPherson, or VITAL-PORT® available from Cook Inc. in Bloomington, Ind. More recently, ports have been used in conjunction with catheters to permit the catheter to be fully implanted. Vascular ports eliminate some of the disadvantages of the externally extending catheters. Since vascular ports are implanted beneath the skin, they eliminate some of the risk of infection. Furthermore, the patient is generally able to engage in most activities, including swimming. However, vascular access ports require a more invasive surgical procedure in order to implant or remove the port in or from the body. Conventional vascular ports require that a large incision be made in the skin and a cavity physically excavated below the skin to receive the port device. Moreover, the port is typically sutured to the muscle fascia. Once the port is in place and the delivery tubing is inserted and directed to the site of application, the incision is closed, leaving a relatively large scar site and protrusion of the skin at the port location. The medication is then delivered to the port transdermally by a needle, which is pushed through the skin and into the chamber of the port through a membrane, such as a silicone membrane. The disadvantage of the port is that it requires an invasive and more time consuming surgical procedure. Therefore, the procedure is, in general, significantly more expensive than the procedure for implanting for conventional externally extending catheters. Furthermore, when the port gets infected, the infection tends to be a large infection and requires similarly invasive procedures for removal of the vascular port.

One difficulty when using conventional ports is that they are hard to connect to the catheter since they often require small clamps to be manipulated in order to seal the catheter onto the port. The use of surgical gloves makes the manipulation of these clamps even more difficult.

In addition, heretofore, ports that are fabricated from all plastic components, though less expensive and easier to fabricate than metal ports or hybrid ports, such as disclosed in U.S. Pat. No. 5,387,192 to Glantz, often do not exhibit effective seals with the membrane. This may result form variations in tolerances of the port parts or from the material characteristics of plastic or a combination of both.

Consequently, there is a need for a vascular access device which can be inserted into the body of a patient with less trauma to the patient, easier to use, and, further, which is easier to manufacture and, therefore, less costly.

SUMMARY OF THE INVENTION

Accordingly, the present invention provides a new and unique vascular access device, which provides a venous and arterial implantable access device designed to permit repeated access to the vascular system for the parenteral delivery of medications, nutritional solutions, and other fluids to selected sites within the vascular system and for sampling of venous blood.

According to one aspect of the invention, a vascular access device includes an implant body having at least one access chamber for receiving medical treatment and a first opening in communication with the access chamber. The implant body has first and second ends and a cannula in communication with the access chamber. The first end is formed by a clamp and is pointed an amount sufficient to separate tissue and, thereby, ease insertion of the implant body through an insertion location, such as an incision, to a placement location remote from the insertion location without excavation of the placement location. A tubular member having at least one lumen extending therethrough is clamped onto the cannula by the clamp to provide communication with the access chamber through the cannula for delivering medical treatment from the access chamber to a preselected treatment site in the body of the patient remote from the placement location. A membrane covers and seals the first opening and is adapted to receive a percutaneous needle puncture without leakage from the puncture.

In one aspect, the second end of the implant body is generally pointed an amount sufficient to separate tissue in order to ease removal of the vascular access device.

In another aspect, the clamp includes a transverse passage formed therein, with the cannula and tubular member positioned in the transverse passage. Preferably, the clamp includes a pair of clamp halves. In one aspect, each of the clamp halves includes a plurality of grooves, which are located in the transverse passage and which induce regions of decreased compression and regions of increased compression between the grooves on the tubular member. The tubular member at least partially extends into the grooves when the clamp halves clamp the tubular member onto the cannula whereby the tubular member is substantially anchored on the cannula by the clamp halves. In other aspects, the clamp halves include a plurality of ribs formed in the transverse passage. The ribs form regions of increase compression at the ribs and regions of reduced compression between the ribs such that the tubular member at least partially extends into the regions between the ribs such that the tubular member is substantially anchored on the cannula by the clamp halves. In yet another aspect, the cannula includes at least one projection, with the projection generating at least one region of increased compression on the tubular member at the projection and regions of reduced compression adjacent the projection such that the tubular member at least partially extends into the regions of the reduced compression whereby the tubular member is substantially anchored on the cannula by the clamp halves.

According to another form of the invention, the vascular access device includes an elongated body having a first and a second end. The second end comprises a closed end, with the first end comprising a clamp. The elongated body is tapered from a medial portion of the elongated body to the first and second ends to form pointed first and second ends to ease insertion or removal of the vascular access device. The elongated body includes an access chamber formed therein for receiving the medical treatment and, further, includes an access opening in fluid communication with the access chamber. A cannula is provided which is in fluid communication with the access chamber. A catheter tube is clamped onto the cannula by the clamp and has a lumen which is in fluid communication with the access chamber of the elongated body through the cannula for delivering medical treatment from the access chamber to a preselected location on the body. A membrane seals the access chamber and is adapted to receive a percutaneous needle puncture without leakage from the puncture.

In one aspect, the clamp comprises a pair of clamp halves. The elongated body preferably includes a landing with the clamp halves being coupled to the landing. In further aspects, the landing extends around the cannula and the clamp halves form a transverse passage therebetween in which the tube is clamped onto the cannula. In other aspects, one of the cannula and the transverse passage includes either projections or recesses to thereby form regions of increased compression and decreased compression on the tube.

According to yet another form of the invention, a vascular access device includes a base portion, which has a chamber, and a top portion, which is mounted to the base portion and includes an access opening which is generally aligned with the chamber. A membrane seals the chamber and is adapted to receive a percutaneous puncture without leakage from the puncture and, further, is accessible through the access opening. A tube is mounted on a cannula, which is in communication with the chamber. A clamp clamps and seals the tube on the cannula. The base, the top portion, and the clamp form an elongated implant body having first and second ends, with the first end comprising the insertion end and being sufficiently pointed to separate tissue when inserted into the body and with the first end being defined by the clamp. In one aspect, the base and the top portion both include a landing, with at least one of the landings including an engagement surface for receiving and engaging a corresponding engagement structure of the clamp to thereby couple the clamp to the top portion and the base portion. In further aspects, the clamp preferably comprises a pair clamps and, more preferably, a pair of clamps which are secured together by welding.

In this manner, the vascular access device can be completely subcutaneously implanted in the body without the extensive surgical techniques associated with conventional ports and, instead, may be implanted with the same ease as a catheter, while providing all the advantages of conventional ports. These and other advantages, benefits, and objects will be understood by one skilled in the art from the drawings, description, and claims which follow.

DESCRIPTION OF THE DRAWINGS

FIG. 5B is a perspective view of the base in FIG. 5A with the cannula removed for clarity;

FIG. 5C is a plan view of the base of FIG. 5B;

FIG. 5D is a side view of the base of FIG. 5B;

FIG. 5E is an end view of the base of the vascular access device;

FIG. 5G is an enlarged perspective end view of the base in FIG. 5F;

FIG. 5H is a cross-section taken along line VI—VI of FIG. G;

FIG. 5I is a similar view to FIG. 5H illustrating another embodiment of the membrane;

FIG. 5J is a similar view to FIG. 5C of a second embodiment of the base of the vascular access device of the present invention;

FIG. 10 is a bottom plan view of the upper clamp half of the vascular access device;

FIG. 11 is a side view of the clamp half of FIG. 10;

FIG. 12 is a top plan view of the clamp half of FIG. 10; and

FIG. 12A is an end view of the clamp half of FIG. 10.

DETAILED DESCRIPTION OF THE PREFERRED EMBODIMENTS

Figure 1:
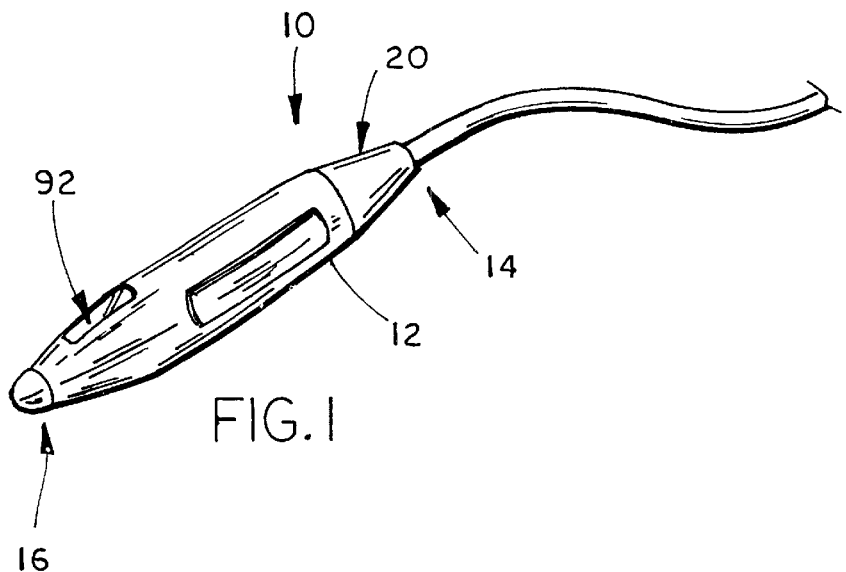
FIG. 1 is a front perspective view of the vascular access device of the present invention.

Referring to FIG. 1, the numeral 10 generally designates a unique vascular access device of the present invention. Vascular access device 10 is preferably implanted by a unique implant procedure, such as described in U.S. Pat. Nos. 5,919,160 and 6,074,377 (which are incorporated by reference herein in their entireties), that can be quickly performed on an outpatient basis. Vascular access device 10 is adapted to permit placement of the device at a placement location through a narrow opening or incision in the patient's skin, which is remote from the placement location. In the event that removal of vascular access device 10 is required, the device can be removed, for example, using a retrieval tool or device (such as disclosed in the above noted patents), again through a narrow opening or incision in the patient's skin.

Figure 4:
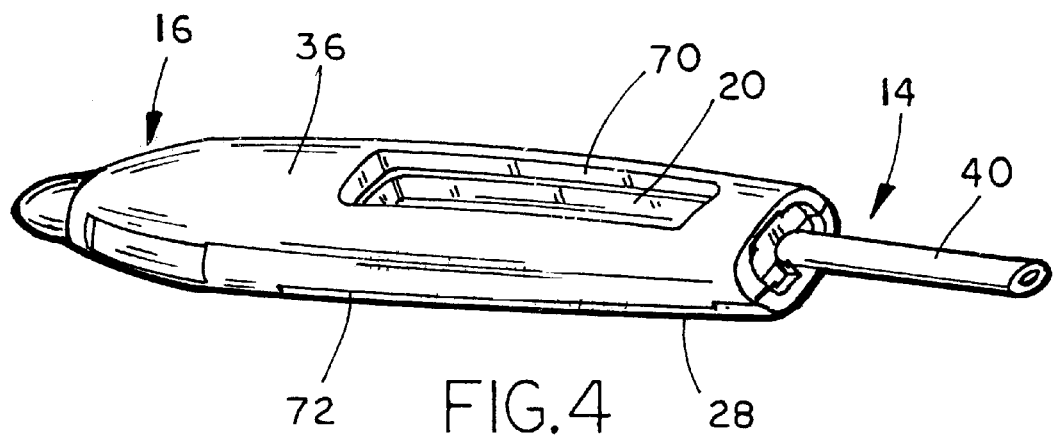
FIG. 4 is an end perspective view of the vascular access device with the clamp halves and membrane removable for clarity.
Figure 5A:
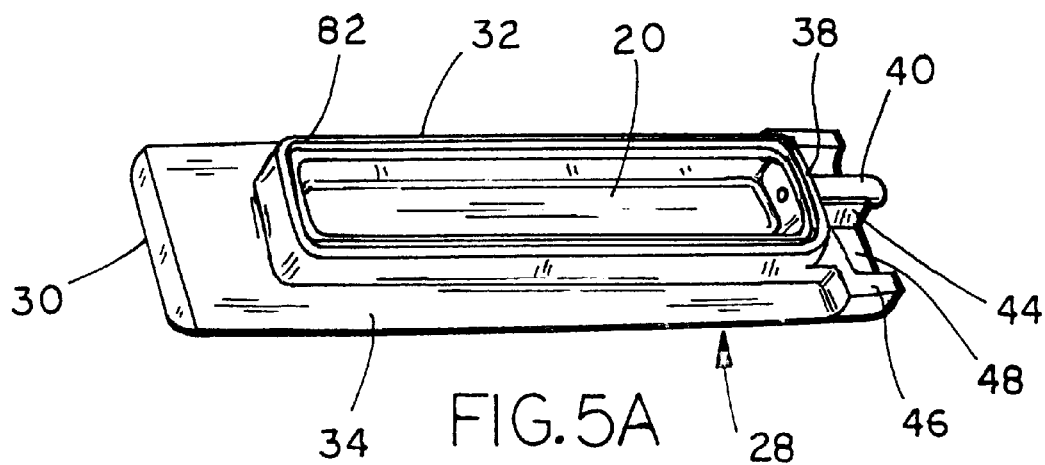
FIG. 5A is a top perspective view of a base of the vascular access device.
Figure 5F:
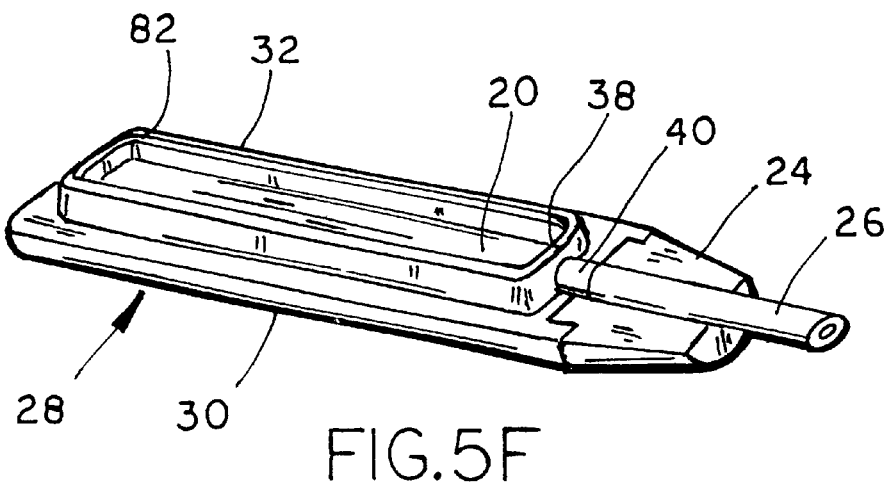
FIG. 5F is an end perspective view of the base of FIG. 5A with a bottom lamp half coupled to the base.

As best seen in FIG. 1, vascular access device 10 includes an implant body 12 having a first end 14 and a second end 16. At least one access chamber 20 (e.g. see FIG. 4) is formed within implant body 12 and is adapted to provide a fluid impermeable chamber for receiving a treatment fluid, as will be more fully described below. First end 14 of implant body 12 defines an insertion end and is formed by a clamp 20 which is tapered and pointed an amount preferably sufficient to separate tissue when device 10 is inserted into the patient's body through the opening or incision. Once inserted into the patient's body through the incision device 10 is urged to the placement location, for example by an elongate tool or finger.

Preferably, clamp 20 comprises a frusto-conical shaped clamp and includes a pair of clamp halves 22 and 24 (FIG. 3), which together clamp on a tubular member 26, such as a catheter tube, onto implant body 12, as will be more fully described below. Tubular member or delivery tube 26 is preferably a silicone catheter and includes a lumen extending therethrough for communicating with the access chamber 20 so that the fluid in access chamber 20 may be delivered by delivery tube 26 to the appropriate vein, organ, or other preselected treatment site within the body of the patient.

Referring to FIGS. 4 and 5A–5F, implant body 12 includes a base or base portion 28, and an upper or top portion 36. Base portion 28 includes a generally flat resting surface 30 (FIG. 5E) on its lower side and an upstanding rectangular-shaped perimeter flange 32 on its upper side which defines therein chamber 20. Base portion 28 also includes perimeter flange which defines a landing surface 34 for supporting top or upper portion 36, which together with base portion 28 and clamp halves 22 and 24 form body 12. Upstanding perimeter flange 32 includes an intermediate reinforced wall section 38 which includes a transverse opening 39 (FIG. SB) through which a cannula 40 (FIG. SA) communicates with chamber 20. Cannula 40 is preferably molded in intermediate wall 38 and, more preferably, includes a flange 42 (FIGS. 4B and 4C) and, more preferably, a tapered flange, to anchor cannula 40 in wall 38.

Figure 4A:
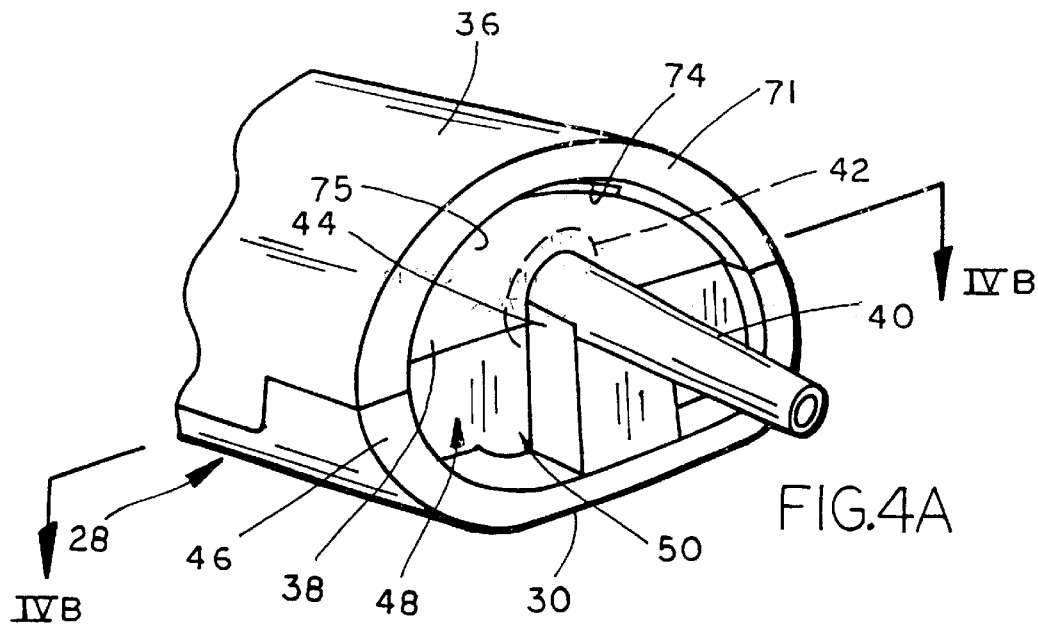
FIG. 4A is an enlarged end view of the vascular access device illustrated in FIG.4.
Figure 4B:
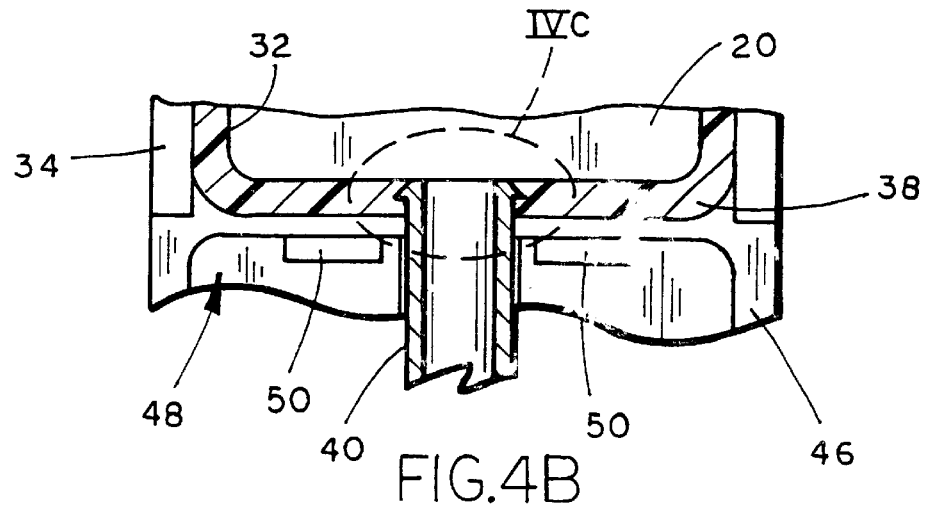
FIG. 4B is a cross-section view taken along line VB—VB of FIG. 4A illustrating the vascular access cannula.
Figure 4C:
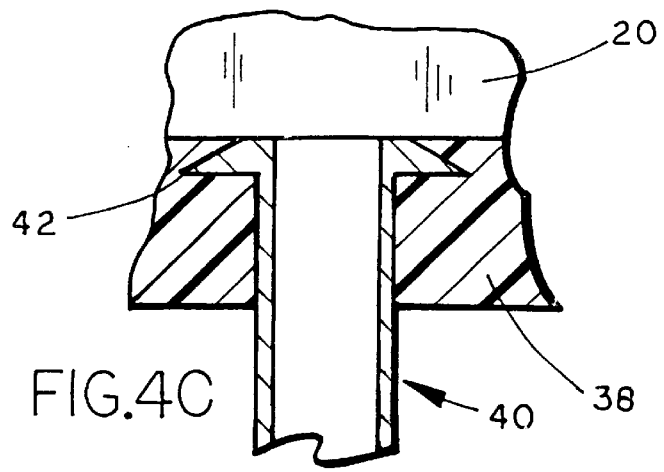
FIG. 4C is an enlarged view of the area designated IVC in FIG. 4B.
Figure 6:
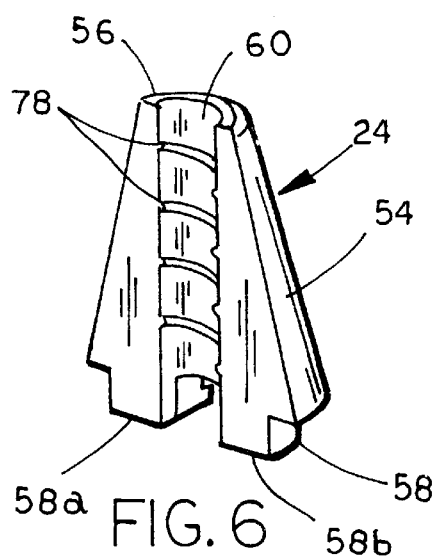
FIG. 6 is an enlarged perspective view of a lower clamp half of the vascular access device.
Figure 7:
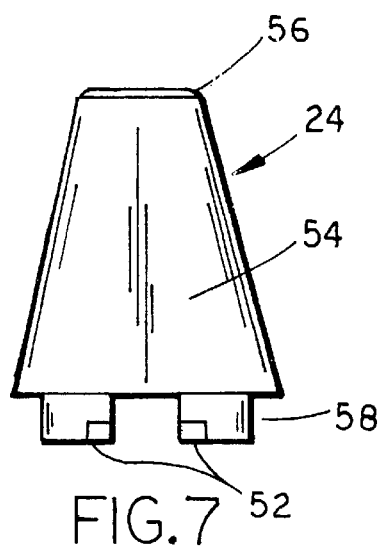
FIG. 7 is a bottom plan view of the clamp half of FIG. 6.
Figure 8:
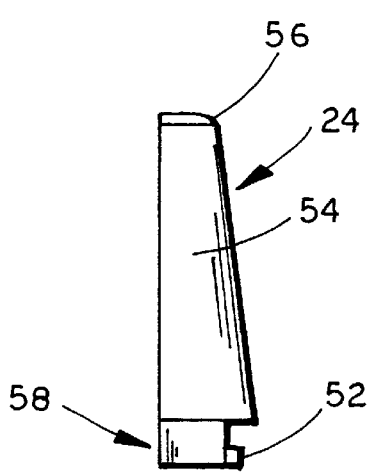
FIG. 8 is a side view of the clamp half of FIG. 6.
Figure 9:
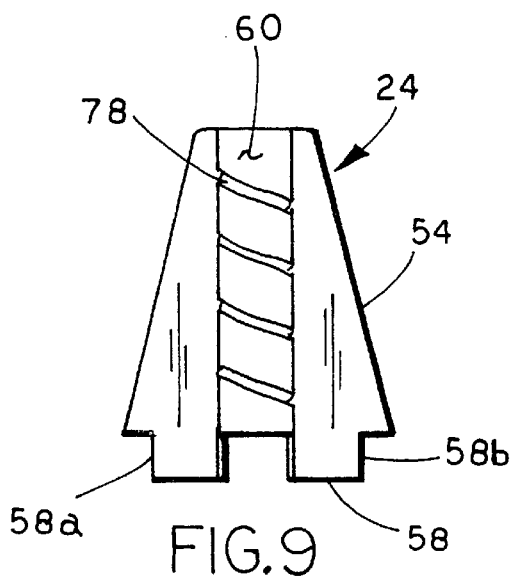
FIG. 9 is a top plan view of the clamp half of FIG. 6.
Figure 9A:
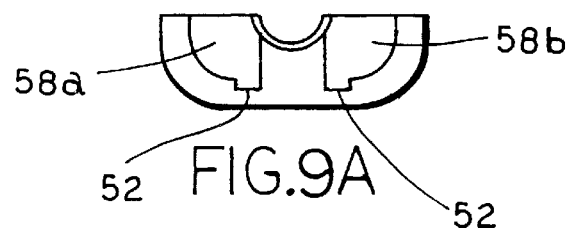
FIG. 9A is an end view of the clamp half of FIG. 6.

As best seen in FIG. 4A, cannula 40 projects outwardly from wall 38 for coupling to tube 26 (FIGS. 5F and 5G) and is preferably at least partially supported by a cannula support or saddle 44 formed in base 28. Base 28 also includes a semi-annular flanged portion 46 which projects outwardly from base 28 and provides a landing 48 for clamp half 24. Flanged portion 46 includes a pair of recess portions or grooves 50. Grooves 50 are positioned on either side of cannula support 44 and receive and engage with corresponding tabs or flanges 52 of clamp half 24.

Referring to FIGS. 6–9 and 9A, clamp half 24 includes a tapered or pointed body 54 extending from a first end 56 to a second end 58, which includes a reduced diameter neck formed from a pair of arcuate flanges 58a and 58b. Mounting flanges 50 are provided on flanges 58a and 58b and engage grooves 50 when clamp half 24 is inserted or rotated into landing 48. Extending from the first end 56 to second end 58 of body 54 is an arcuate or semicircular transverse groove 60 which together with a corresponding arcuate or semi circular transverse groove 62 (FIG. 10) of clamp half 22 forms a transverse passage 64 and an opening 66 through which tube 26 extends to couple and be clamped onto cannula 40.

Referring to FIGS. 10–12 and 12A, clamp half 22 similarly includes a tapered or pointed body 66 with a reduced diameter neck 68 for mounting onto body 12. Referring again to FIG. 4A, upper portion 36 of body 12 includes a semi-annular projecting flange 71 which together with wall 38 forms a recessed landing 75 for clamp half 22. When seated on landing 75, clamp half 22 rests on clamp half 24. In addition, as best seen in FIG. 4A, flange 71 includes an elongated groove or recessed portion 74 to receive and engage a corresponding mounting flange 76 (FIGS. 11, 12, and 12A) of clamp 22. Thus, when the neck portions of clamp halves 22 and 24 are positioned in recessed landings 48 and 75, clamp halves 22 and 24 are interlocked with body 12 and, further, define transverse passage 64 for receiving tube 26. Preferably, once tube 26 is positioned over cannula 40, and clamp halves 22 and 24 are interlocked with body 12, clamp halves 22 and 24 are secured together, for example by welding to clamp tube 26 onto cannula 40. As a result, clamp halves 22 and 24 not only clamp and seal tube 26 on cannula 40 but they also provide support to cannula 40. As is understood in the art, the stresses at a connector, such as at a cannula, to a port are much higher than other parts of the port and, thus, tend to form one of the failure modes of the port. By incorporating the clamp as part of the implant body, the present vascular access device exhibits significantly lower stresses at the cannula connection to the body, thus increasing the durability of the vascular access device and reducing the risk of leakage which can result from a weakened connection between the cannula and device body.

Referring again to FIGS. 6 and 10, grooves 60 and 62 each include semi-annular grooves 78 and 80, respectively, which preferably substantially align to form a spiral or helical groove which extends through passageway 64. In this manner, when clamp halves 22 and 24 are secured together, the space between grooves 78 and 80 provide regions of increased compression on tube 26, which causes tube 26 to at least partially extend into grooves 78 and 80 to thereby provide additional axial restraint to tube 26 beyond the friction between tube 26 and cannula 40. Alternately, each transverse groove 60, 62 may include annular ribs to provide increased local compression in tube 26 thus causing tubular member 26 to exhibit some localized deformation again with tubular member 26 partially extending into the space between the ribs.

Implant body 12 further includes an access opening 70 formed in upper member 36, which aligns with chamber 20 to permit transdermal access to chamber 20.

Access opening 70 extends longitudinally relative to body 12 and extends over chamber 20 and a selectively permeable closure membrane 84, which is adapted to receive a percutaneous needle puncture without leakage from the puncture. Implant body 12, access chamber 38, delivery tube 26, membrane 84, and clamp halves 22 and 24 cooperate to provide a fluid impermeable vascular access device 10 which may receive, without leakage, a medical treatment fluid such as chemotherapy agents, pain medication, and the like. Referring to FIGS. 5D and 5E, upstanding flange 32 preferably includes a raised inner perimeter ridge 82 which together with flange 32 provides a mounting surface for a membrane 84, which extends over flange 32 to seal chamber 20.

In order to ease removal of device 10, second end 16 of implant body 12 is also generally pointed an amount sufficient to separate tissue when removing device 10 and, further, preferably includes an engagement structure 92 for engagement by a retrieval tool, such as previously mentioned and described in U.S. Pat. Nos. 5,919,160, and 6,074,377. Vascular access device 10 is typically removed from the patient, such as when vascular access device 10 is no longer needed, when access device 10 needs to be replaced or serviced, or the like. In preferred form, engagement structure 92 is formed in upper portion 36 and, preferably, comprises a depression or recess that can be engaged by the retrieval tool. Optionally, engagement structure 92 may include a transverse opening which extends through second end 16. Preferably, second end 16 includes guide surfaces to ease location of engagement structure 92, such as tapered groove or the like.

Figure 2:
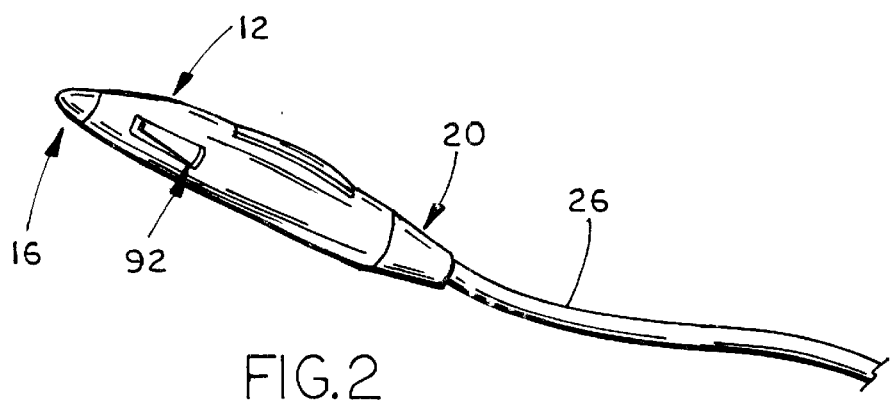
FIG. 2 is a side perspective view of the vascular access device of FIG. 1.
Figure 3:
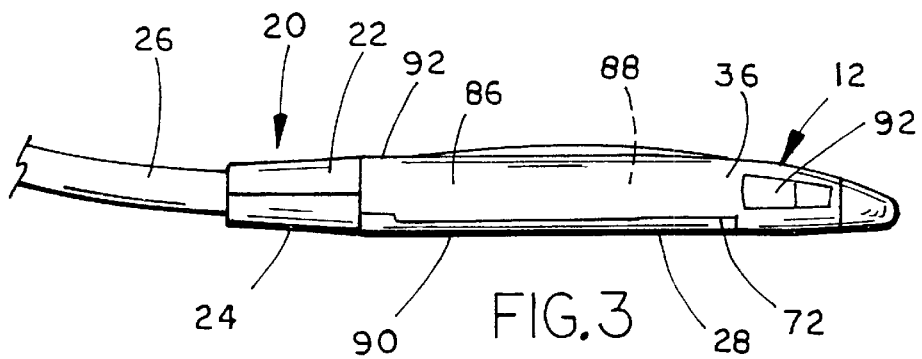
FIG. 3 is a side elevation of the vascular access device of FIG. 1.

As best seen in FIGS. 1, 2, and 3, implant body 12 of vascular access device 10 includes a low-profile unitary body having a pair of laterally spaced sidewalls 86 and 88, a spanning bottom wall 90, formed by base 28, and a top wall 92, formed by upper portion 36. Upper portion 36 includes a recessed portion 72 which receives base 28 to form an interlocking assembly with base 28. Implant body 12 is preferably elongated and roughly cylindrical in shape and, preferably, has a length of approximately two and one-quarter inches and a width of approximately between one-quarter and three-eighths inch. Preferably, the length of implant body 12 is between approximately four and seven times the width of implant body 12. The low profile of implant body 12 permits vascular access device 10 to be readily placed under the skin of the patient through a small incision. In addition, bottom wall 90 is preferably generally flat or otherwise includes flattened regions in order to stabilize vascular access device 10 from rolling over once implanted under the skin of the patient.

One preferred method of assembly of vascular access device 10 is best understood from FIGS. 4 and 5A–5H. Base 28 is preferably molded from a plastic material with cannula 40, which is preferably a metal cannula, molded in wall 38. Membrane 84 is mounted on flange 32, with a portion of membrane 84 extending inwardly toward chamber 20 (see FIG. 5H) between ridge 82, with the portion partially extending into chamber 20 being compression fit between the sides and ends of ridge 82. Top or upper portion 36, which is also similarly preferably molded from a plastic material, is placed over membrane 84 and positioned on landing 34 of base 28. Once in place, top portion 36 is preferably secured to base 28, for example by welding or an adhesion or the like. In this manner, instead of relying on the compression between the top portion and the base of the vascular access device to seal membrane 84, membrane 84 relies on the compression of the membrane within ridge 82 to seal chamber 20. In addition, given the compression fit arrangement, membrane 84 is self sealing and seals punctures from needles accessing the vascular access device. Optionally before welding, clamp half 24 may be positioned on landing 48, with mounting flanges 52 being engaged with grooves 50. Tube 26 is then preferably mounted on the end portion of cannula 40. Once tube 26 is mounted on cannula 40, second clamp 22 is aligned with landing 75 and with groove 62, which is aligned over tube 26 and cannula 40. Grooves 62 and 60 thereby form transverse passageway 64. Once in place, clamp half 22 is preferably secured to clamp half 24 and, further, optionally to upper portion 36 and base 28, such as by welding. Alternately, upper portion 36 may be welded to base 28 after clamp halves 22 and 24 are in position to assure a proper alignment of all the component parts.

Referring to FIG. 5I, membrane 84' may be injection molded with base 28 or otherwise attached to base 28 such that membrane 84' is supported at its perimeter but with negligible radially inward compression. Instead of relying on the inward compression forces to seal punctures (as compared to membrane 84), membrane 84 relies on the pressure of the fluid to seal punctures, especially for punctures which are introduced by angled needles.

In another preferred embodiment of the base 128 of the vascular access device illustrated in FIG. 5J, cannula 140 includes a pair of projections 142 formed or mounted thereon. In preferred form, projections 142 comprise annular projections and may be either formed as part of cannula 140 or may comprise O-ring seals which are mounted onto cannula 140. As would be understood, projections 142 increase the compression over localized areas or regions on tube 126, which is mounted on cannula 140 over the projections. In addition, the clamp halves (only 124 shown) may include corresponding grooves 124a to receive at least a portion of projections 142 to thereby provide further axial restraint of tube 126 on the device body.

It should be understood from the foregoing that the vascular access device as disclosed herein may be used for chronic venous or organ access. The implanted device facilitates repeated intermittent infusions of chemotherapeutic agents, medicines, such as those drugs used for therapy, nutritional fluids, blood products as well as blood sampling. Furthermore, as the access device includes an elongated shape having first and second generally pointed ends, the insertion and removal of the device is far simpler than the prior known devices and provides the same advantages of the portal devices but without the need for the extensive surgery that is required with prior known portal devices. Furthermore, the vascular access device of the present invention offers the advantages of the conventional externally extending catheter but with reduced risk of infection as the device does not extend externally of the body.

While the preferred embodiment is described in terms of a human patient, the invention may also be used with an animal patient as well. Further, the invention may alternatively be used to introduce treatment materials other than fluids into the patient, such as, for example, a wire lead or other type of implant.

It is to be understood that the foregoing is a description of the preferred embodiments. One skilled in the art will recognize that variations, modifications, and improvements may be made without departing from the spirit of the invention disclosed herein. For example, similar to the vascular access device may include two or more access chambers to supply more than one medicant and/or tactile identification structures, such as disclosed in U.S. Pat. Nos. 5,919,160 and 6,074,377. The scope of the protection afforded is to be measured by the claims which follow and the breadth of interpretation which the law allows.

I claim:

1. A clamp for a vascular access device, the vascular access device for inserting into a body of a patient through a point of insertion and being adapted to be located to a placement location remote from the point of insertion of the vascular access device and, further, being adapted to be used for periodic delivery of medical treatment to a treatment site in the body of the patient remote from the placement location, the vascular access device having an implant body having at least one access chamber formed therein and a first opening in communication with the access chamber, the implant body having a membrane sealing the first opening and an inserting end, said clamp comprising:

a clamp body including a pair of clamp halves, said clamp body being adapted to form the insertion end of the vascular access device and to couple to the implant body to form part of the implant body, said clamp body being pointed an amount sufficient to separate tissue and ease insertion of the vascular device through a point of insertion to a placement location remote from the point of insertion; and said clamp halves being adapted for clamping a tubular member onto a cannula of the vascular access device.

2. The clamp according to claim 1, wherein said clamp halves define therebetween a transverse passage for receiving the cannula and the tubular member therein, each of said clamp halves including a plurality of grooves, said grooves being located in said transverse passage and for inducing regions of decreased compression on the tubular member and for inducing regions of increased compression between said grooves on the tubular member.

3. The clamp according to claim 1, wherein said clamp halves define a transverse passage therebetween, said clamp halves including a plurality of ribs provided in said transverse passage, said ribs for inducing regions of increased compression in the tubular member at said ribs and for inducing regions of reduced compression in the tubular member between said ribs.

4. The clamp according to claim 1, wherein said clamp halves include engagement structures for engaging the implant body.

5. The clamp according to claim 4, wherein said clamp body includes an outer surface being adapted for substantially aligning and for being substantially contiguous with the outer surface of the implant body such that when said clamp body is mounted and coupled to the implant body, said clamp body and implant body form an elongated, tapered body.

6. The clamp according to claim 1, wherein said clamp body comprises a plastic clamp body.

7. The clamp according to claim 1, wherein said clamp body comprises a frustoconical shaped clamp body.

8. A vascular access device for inserting into a body of a patient through a point of insertion, said vascular access device adapted to be located to a placement location remote from the point of insertion of the vascular access device and, further, adapted to be used for periodic delivery of medical treatment to a treatment site in the body of the patient remote from the placement location, said vascular access device comprising:

an implant body having at least one access chamber formed therein and a first opening in communication with said access chamber, said implant body having first and second ends, said first end comprising a clamp, and said clamp being pointed an amount sufficient to separate tissue and ease insertion of said implant body through a point of insertion to a placement location remote from the point of insertion without a site excavation of the placement location;

a cannula in communication with said access chamber;

a tubular member having at least one lumen extending therethrough, said tubular member clamped onto said cannula by said clamp to provide communication between said tubular member and said access chamber for delivery of material from said access chamber along said tubular member to the treatment site in the patient's body; and a membrane covering and sealing said first opening but adapted to receive a percutaneous needle puncture without leakage from the puncture.

9. The vascular access device according to claim 8, wherein said second end is pointed an amount to separate tissue to ease removal of said implant body.

10. The vascular access device according to claim 8, wherein said clamp includes a transverse passage formed therein, said cannula and said tubular member positioned in said transverse passage.

11. The vascular access device according to claim 10, wherein said clamp includes a pair of clamp halves.

12. The vascular access device according to claim 11, wherein each of said clamp halves includes a plurality of grooves, said grooves being located in said transverse passage and inducing regions of decreased compression and regions of increased compression between said grooves on said tubular member, said tubular member at least partially extending into said grooves when said clamp halves clamp said tubular member on said cannula whereby said tubular member is substantially anchored on said cannula by said clamp halves.

13. The vascular access device according to claim 11, wherein said clamp halves include a plurality of ribs formed in said transverse passage, said ribs forming regions of increased compression at said ribs and regions of reduced compression between said ribs such that said tubular member at least partially extends into said regions between said ribs whereby said tubular member is substantially anchored on said cannula by said clamp halves.

14. The vascular access device according to claim 11, wherein cannula includes at least one projection, said projection generating at least one region of increased compression on said tubular member at said projection and regions of reduced compression adjacent said projection such that said tubular member at least partially extends into said regions of reduced compression whereby said tubular member is substantially anchored on said cannula by said clamp halves.

15. The vascular access device according to claim 8, wherein said cannula includes a flange, said flange at least partially embedded in said implant body to anchor said cannula to said implant body.

16. The vascular access device according to claim 11, wherein said implant body further includes a recessed landing extending around said cannula, said clamp halves coupled to said implant body at said recessed landing.

17. The vascular access device according to claim 16, wherein said landing includes engagement structures, and said clamp halves including corresponding engagement structures for engaging said engagement structures of said landing to thereby couple said clamp halves to said implant body.

18. The vascular access device according to claim 17, wherein said engagement structures of said landing comprise grooves.

19. A vascular access device according to claim 8, wherein said second end includes a receiving structure adapted for engaging a cooperating structure of a retrieval device.

20. A vascular access device according to claim 19, wherein said receiving structure comprises an indent.

21. A vascular access device according to claim 11, wherein said clamp halves are welded together.

22. The vascular access device according to claim 8, wherein said clamp includes an outer surface, said implant body having an outer surface, said outer surface of said clamp being substantially aligned and contiguous with said outer surface of said implant body whereby said clamp and said implant body form an elongated, tapered body.

23. The vascular access device according to claim 8, wherein said membrane generally follows the contour of an outer surface of said implant body.

24. The vascular access device according to claim 8, wherein said implant body comprises an elongate implant body.

25. The vascular access device according to claim 8, wherein said implant body comprises a plastic implant body.

26. A vascular access device for inserting into the body of a patient, said vascular access device for delivering medical treatment to a preselected location in the body of the patient, said vascular access device comprising:

an elongated body having a first end and a second end, said second end comprising a closed end, said first end comprising a clamp, said elongated body being tapered from a medial portion of said elongated body to said first and second ends to form pointed first and second ends to ease insertion of and removal of said vascular access device, said elongated body including an access chamber formed therein for receiving the medical treatment, said elongated body further including an access opening in fluid communication with said access chamber;

a cannula in fluid communication with said access chamber;

a catheter tube clamped onto said cannula by said clamp and having a lumen extending therethrough, said lumen of said catheter tube in fluid communication with said access chamber of said elongated body through said cannula for delivering medical treatment from said access chamber of said elongated body to the preselected location in the body; and a membrane sealing said access opening, and said membrane being adapted to receive a percutaneous needle puncture without leakage from the puncture.

27. The vascular access device according to claim 26, wherein said clamp comprises a pair of clamp halves, said elongated body having a landing, said clamp halves coupled to said landing.

28. The vascular access device according to claim 27, wherein said landing extends around said cannula, said clamp halves forming a transverse passage therebetween, and said tube being clamped onto said cannula in said transverse passage.

29. The vascular access device according to claim 28, wherein one of said cannula and said transverse passage includes a plurality of one of projections and recesses to thereby form regions of increased compression and decreased compression on said tube.

30. The vascular access device according to claim 29, wherein said transverse opening includes said plurality of one of projections and recesses.

31. The vascular access device according to claim 30, wherein said second end includes an engagement surface for engagement by a corresponding engagement structure on a retrieval tool.

32. The vascular access device according to claim 26, wherein said clamp comprises a frusto-conical shaped clamp.

33. A vascular access device for inserting into a body of a patient through a point of insertion, said vascular access device adapted to be located to a placement location remote from the point of insertion of the vascular access device and, further, adapted to be used for periodic delivery of medical treatment to a treatment site in the body of the patient remote from the placement location, said vascular access device comprising:

a base portion having a chamber;

a top portion being mounted to said base portion and having an access opening, said access opening generally aligning with said chamber;

a membrane sealing said chamber and being adapted to receive a percutaneous puncture without leakage from the puncture, and said membrane being accessible through said access opening;

a cannula in communication with said chamber;

a tube mounted on said cannula and in communication with said chamber through said cannula; and a clamp clamping and sealing said tube on said cannula, said base, said top portion, and said clamp forming an elongated implant body having first and second ends, said first end comprising an insertion end and being sufficiently pointed an amount to separate tissue when inserted into the body of the patient, and said first end being defined by said clamp.

34. The vascular access device according to claim 33, wherein said base portion, said top portion, and said clamp comprise plastic members.

35. The vascular access device according to claim 33, wherein said clamp includes a pair of clamp halves.

36. The vascular access device according to claim 35, wherein each of said clamp halves each having a transverse groove, said transverse grooves forming a transverse passage, said tube and said cannula being positioned in said transverse passage.

37. The vascular access device according to claim 36, wherein each of said clamp halves includes a plurality of grooves, said grooves being located in said transverse passages and inducing regions of decreased compression and regions of increased compression between said grooves on said tube, and said tube at least partially extending into said grooves when said clamp halves clamp a tube on said cannula whereby said tube is substantially anchored on said cannula by said clamp halves.

38. The vascular access device according to claim 33, wherein each of said base portion and said top portion includes a landing, at least one of said landings including an engagement structure for receiving and engaging a corresponding engagement structure of said clamp to thereby couple said clamp to said top portion and said base portion.

39. The vascular access device according to claim 38, wherein said clamp comprises a pair of clamp halves.

40. The vascular access device according to claim 39, wherein said clamp halves are secured together by welding.

* * * * *

UNITED STATES PATENT AND TRADEMARK OFFICE
CERTIFICATE OF CORRECTION

PATENT NO. : 6,468,252 B1  Page 1 of 1
APPLICATION NO. : 09/631847
DATED : October 22, 2002
INVENTOR(S) : Dominic J. Sanfilippo, II It is certified that error appears in the above-identified patent and that said Letters Patent is hereby corrected as shown below:

Column 5:
Line 6, "lamp" should be --clamp--.

Column 6:
Line 18, "FIG. SB" should be --FIG. 5B--.
Line 18, "FIG. SA" should be --FIG. 5A--.

Signed and Sealed this

Thirtieth Day of January, 2007

JON W. DUDAS
*Director of the United States Patent and Trademark Office*